(12) United States Patent  (10) Patent No.: US 7,191,783 B2
Russell  (45) Date of Patent: Mar. 20, 2007

(54) SYSTEM, METHOD, AND APPLIANCES FOR APPLYING HAIR TREATMENTS

(75) Inventor: Marsha A Russell, Salem, MA (US)

(73) Assignee: PWAI, LLC., Salem, MA (US)

( * ) Notice: Subject to any disclaimer, the term of this patent is extended or adjusted under 35 U.S.C. 154(b) by 112 days.

(21) Appl. No.: 10/738,059

(22) Filed: Dec. 17, 2003

(65) Prior Publication Data

US 2004/0129287 A1   Jul. 8, 2004

Related U.S. Application Data

(63) Continuation-in-part of application No. 10/329,815, filed on Dec. 23, 2002, now Pat. No. 6,863,076.

(51) Int. Cl.
*A45D 2/00*   (2006.01)

(52) U.S. Cl. .................................... 132/222

(58) Field of Classification Search ................ 132/222, 132/208, 270, 221, 207
See application file for complete search history.

(56) References Cited

U.S. PATENT DOCUMENTS

| | | | |
|---|---|---|---|
| 757,204 A | 4/1904 | Koenig | |
| 2,475,998 A | 7/1949 | Soergel | |
| 2,524,266 A * | 10/1950 | Licastro | ...................... 132/246 |
| 3,304,945 A | 2/1967 | Anderson | |
| 4,196,741 A | 4/1980 | Minghenelli | |
| 4,403,622 A | 9/1983 | Stahl | |
| 4,552,159 A | 11/1985 | Fabbri et al. | |
| 4,655,377 A | 4/1987 | Orangeo, Jr. et al. | |
| 5,007,443 A | 4/1991 | Fulgoni | |
| 5,056,539 A * | 10/1991 | Abramson | ................... 132/270 |
| 5,058,609 A | 10/1991 | Sandoz et al. | |
| 5,156,172 A | 10/1992 | Tancredi | |
| 5,287,864 A | 2/1994 | Gallo | |
| 5,335,679 A | 8/1994 | Baxter | |
| 5,549,126 A | 8/1996 | Green | |
| 5,799,669 A | 9/1998 | Briggs | |
| 5,849,421 A * | 12/1998 | Stephan | ...................... 428/603 |
| 5,860,431 A | 1/1999 | Abercrombie et al. | |
| 5,931,168 A | 8/1999 | Abercrombie et al. | |

OTHER PUBLICATIONS

PCT International Search Report dated Aug. 17, 2004 of International Application No. PCT/US03/39997 filed Dec. 17, 2003.

* cited by examiner

*Primary Examiner*—John J. Wilson
*Assistant Examiner*—Robyn Doan
(74) *Attorney, Agent, or Firm*—Maine & Asmus

(57) ABSTRACT

A hair foil and hair holding system for applying hair treatments has a hair anchoring strip close to or aligned with the leading edge of a foil or hair holding appliance, by which it is adhered to the scalp in a hands-free, non-lifting relationship. The strip may be the hook component of a hook and loop fabric fastener system. The leading edge may be pinked to provide a pattern of slots for access for picking and placing hair strands on the foil. The appliance may have provision for attaching a foil blank. The foils may have shoulders extending out wider than the leading edge is long. The foils may have flaps to aid in urging them forward with a pick during usage. The foils or appliances may be made from continuous webs of leading edge or foil material and hair anchoring material.

4 Claims, 10 Drawing Sheets

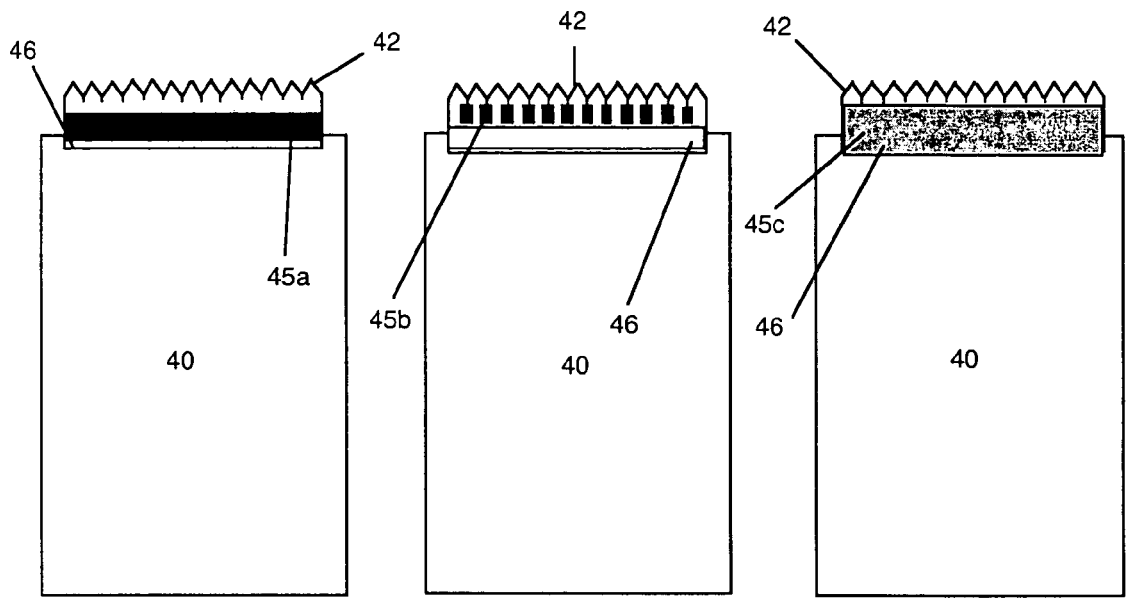
Fig. 4a  Fig. 4b  Fig. 4c
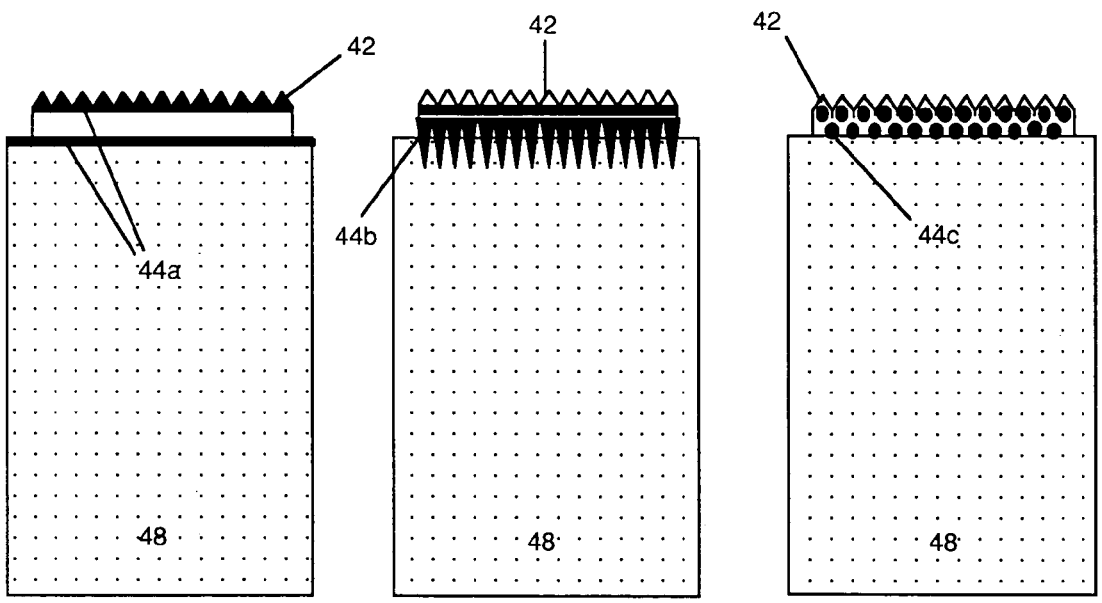
Fig. 5a  Fig. 5b  Fig. 5c
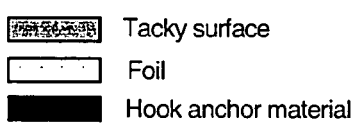 Tacky surface
Foil
Hook anchor material

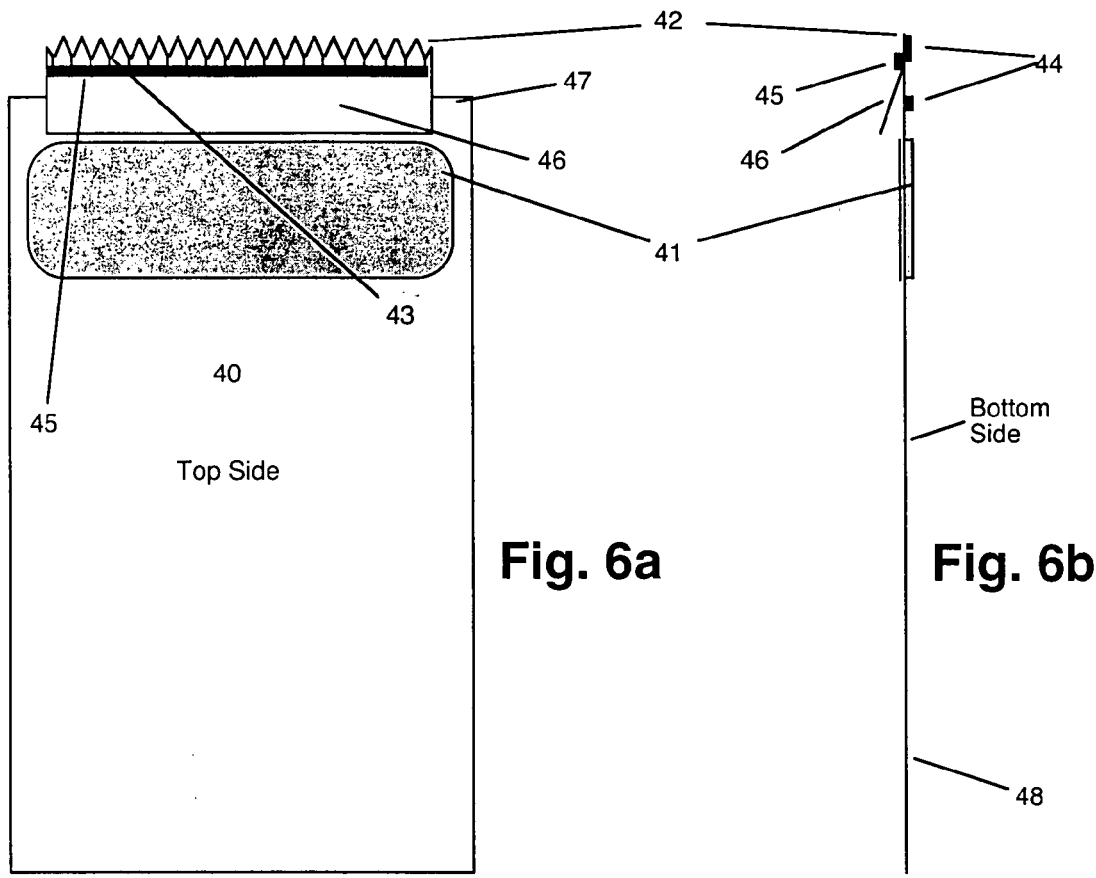
Fig. 6a
Fig. 6b
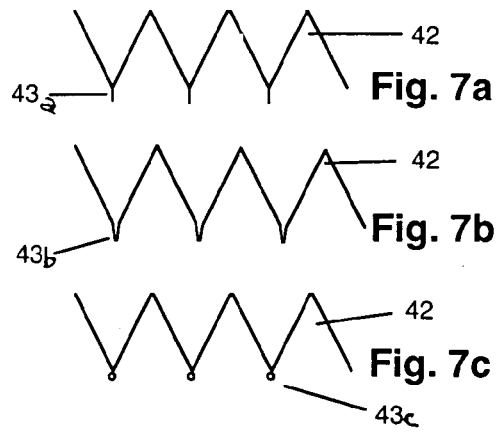
Fig. 7a
Fig. 7b
Fig. 7c
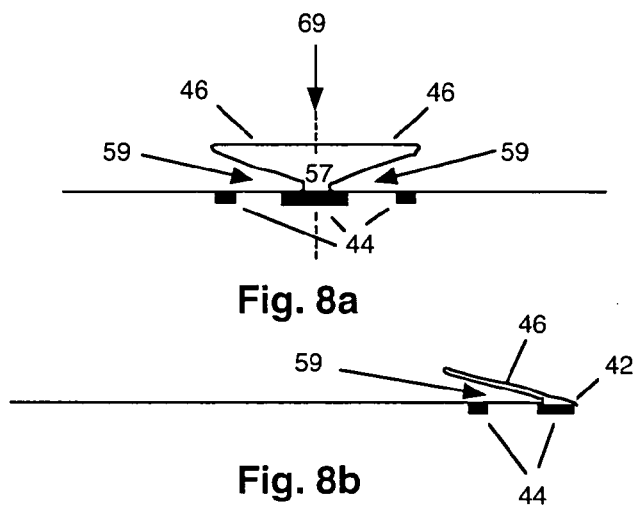
Fig. 8a
Fig. 8b
☐ Color Cell
■ Hook anchor material

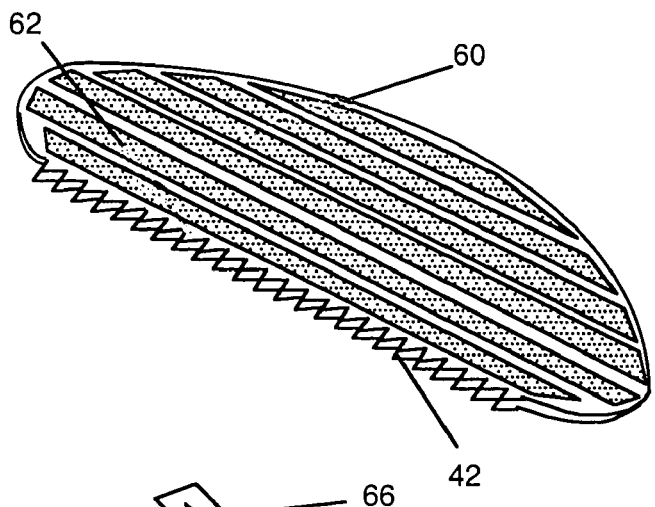
Fig. 9
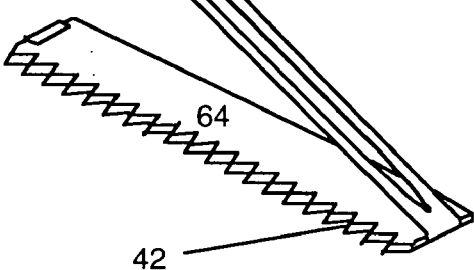
Fig. 10
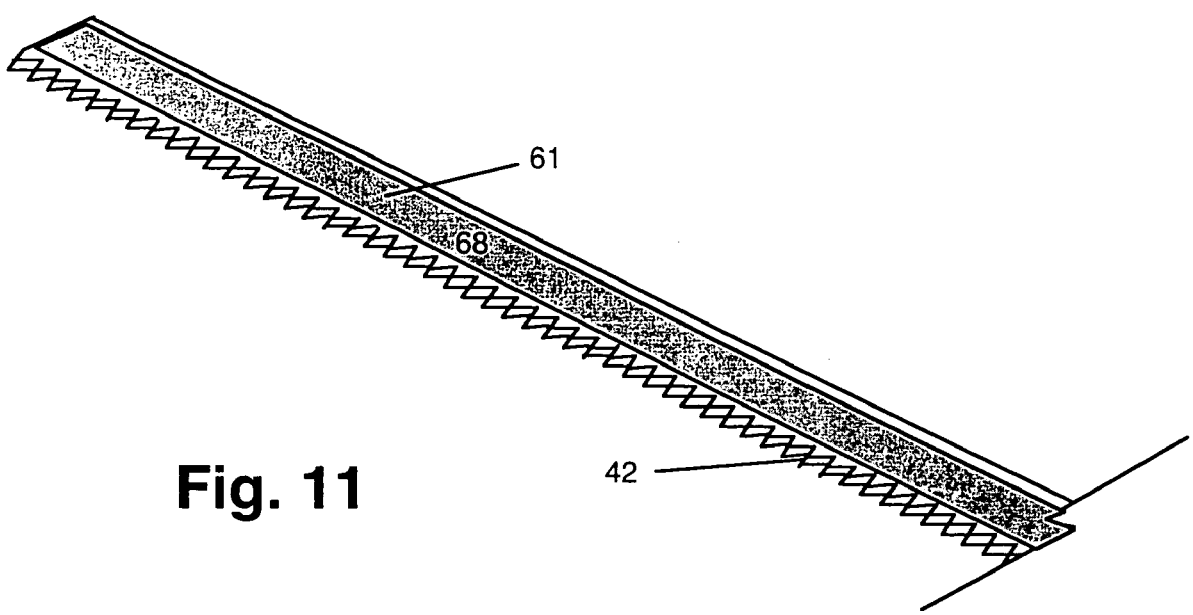
Fig. 11
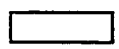 Tacky Surface or Adhesive
 Hook Anchor material

SYSTEM, METHOD, AND APPLIANCES FOR APPLYING HAIR TREATMENTS

This invention is a continuation in part, relates, and claims priority to pending U.S. application Ser. No. 10/329,815, filed on Dec. 23, 2002, now U.S. Pat. No. 6,863,076.

FIELD OF THE INVENTION

The present invention relates to systems, methods and appliances for applying fluid treatments to a head of hair, and in particular to such systems, methods and appliances including modified foils with hair parting and gripping features and other hair holding appliances for applying a hair processing treatment to a person's hair.

BACKGROUND OF THE INVENTION

The present invention is directed to the technology of altering the appearance and texture of people's hair, including such commonly practiced processes as coloring, lighting, frosting, straightening, and waving hair. These techniques are used to change the color and general appearance of a person's hair. In particular, frosting and highlighting treatments involve the coloring of selected strands of hair on the subject's scalp, while leaving other strands their natural color, or another color. Such selective coloring techniques are by nature time consuming and expensive.

A number of different methods have been used by cosmetologists and hair professionals to accomplish such treatments in the prior art. One of the most common involves the use of what is referred to as a "foil". The hair is typically parted along a selected part line and laid down to either side of the part line. Using other hand tools and appliances, selected strands of hair along the part line are manually pulled out in a technique called "weaving". A paper or foil, typically a small rectangular sheet of chemical-impervious material, is laid on the underside of the part line with one edge aligned with the part line, substantially covering the hair on that side of the part line. The selected strands of hair are laid down on the foil such that the foil provides a chemical and/or fluid barrier between the selected strands and the underlying hair and scalp. Coloring chemicals are then carefully applied to the selected strands, using a brush, foam, or sponge. The trailing half of the foil is then folded over towards the leading edge and tends to be held there by the adhesive quality of the chemical so as to sandwich the selected strands within the folded foil, permitting the color chemical agent to be absorbed by the hair strands for maximum affect. The foil may be folded yet again and secured in the double folded position to gain a better grip on the entrapped strands of hair. The position of the foil is dependent on the folded foil's grip on the selected strands of hair.

The process is repeated with a new part line and a new foil for each area of the scalp and hair intended to be treated. Eventually, dozens or more separate foils may cover the subject's head, and these are left in place for a time while the coloring agents do their work. Finally, the foils are removed and disposed of.

The foil method is inexpensive as far as the cost of the foil materials are concerned, but it is extremely time consuming, thereby limiting the number of clients a stylist or hair professional can serve, which results in a high cost to each client. The foils are typically made of a coated metal foil material, from which they got their name, but may be just paper or coated paper. They may be cut to the desired size for each area of the subject's head to be treated. More importantly, the hair stylist must use one hand to hold the selected strands of hair and the other hand to pick and place the foil. After the strands are selected and laid in place on the foil, the stylist, still holding the foil in one hand, applies the coloring agent with the other hand to the strands.

The process is awkward, requires concentration, is tiring with repetition. The technique requires the stylist to keep all the materials required within easy reach. Only after the foil has been folded and refolded and is apparently being held by the stickiness of the applied chemicals, can the stylist's hands be released to begin the next foil. The folded foil's position on the scalp is then maintained by its multiple fold grip on the selected strands near their respective root ends at the part line at the leading edge of the foil.

Even when the stylist is practiced and careful, the foil may move about on the scalp during the application of the coloring agent, resulting in delay, difficulty in selecting the desired strands, the coloring of other, undesired portions of hair, excess exposure of the scalp to the chemicals, or longer than necessary root ends that are not enclosed by the folded foil and not effectively colored. In addition, there exists the danger of seepage of the coloring agent from the folded foil, causing similar problems.

Furthermore, because of the overall time and complexity involved in this process, the stylist often has difficulty in managing the details of the process; in maintaining each consecutively placed foil with its coloring agents for the desired uniform time interval in order to maintain a consistent coloring effect for the client. There remain further persistent problems of the process chemicals reacting with the metallic or other substances in the foil, and of coloring too much or too little of the hair, due, in part, to the timing problems relating to individual foils and the varying effects on the hair color.

Other methods of administering chemical hair treatments have been used in order to attempt to circumvent the problems of the foil method. These include covering the subject's hair with a cap having a number of holes formed within, and pulling strands of hair through the holes using a hook or other suitable device. A coloring agent can then be applied to the strands extending through the cap. However, this method has a number of problems associated, not the least of which that it is painful for many subjects.

There are a myriad of other common tools and devices for use with hair management. One example of a common tool for hair retention and for retaining other objects such as hats to the hair and head is the common "bobby pin", a simple wire spring clip with a small V throat and small knobby wire ends for pushing into the hair. Other hair and head ornaments such as barrettes and hair bands, unrelated to the instant technology, are known to have smooth teeth to aid in retaining lateral placement in the hair. However, these devices all, inevitably, rely on an additional component of retention to prevent simple lifting of the device out of the hair. For example, consider the length and over curvature of a flexible hair band which is sprung open for placement and relies on its spring-like squeezing of the device around the wearer's skull; or the barrette, which incorporates an underside hairclip to gather and squeeze a large bundle of hair against the bottom of the barrette.

Clearly, there is room in the art and technology of chemical hair treatment for improvements in the associated systems, methods and appliances.

SUMMARY OF THE INVENTION

The present invention relating to hair treatments, including the system, tools and methodology, provides substantial advances over the problems of the prior art hair processes and products. It is among the goals of the invention to provide that the advantages of the conventional foil method are maintained or improved, including the relatively low cost and simplicity of use of the foils themselves. It is a further goal to reduce the level of skill and concentration required. It is another goal to improve the quality of the professional stylist's work. It is a yet further goal that the total time required to place the same number of foils be reduced significantly, improving the stylist's productivity.

It is an object of the present invention to provide improved foils and related appliances for weaving and applying chemical hair treatments which will accelerate and simplify the process for both amateur and professional hair stylists, bringing greater ease and efficiency to the over all process.

To these ends, there is provided an improved foil which upon placement on the combed hair at one side of a part line immediately clings to the combed hair, before or after hair strands are selected for treatment, so that the stylist is free to use both hands to a greater extent in conducting the weaving and chemical treatment, or to move about during the application if necessary. Hair strands may be selected and picked along the leading edge of the hair foil from among the combed hair beneath the emplaced foil. After the strands are selected and laid on the foil, it maintains the selected strands in place before the foil is folded, so that constant adjustment of the strands, as in the prior art, is not required. The result is that the chemical hair treatment process using the foils of the present invention proceeds at a fraction of the time required by method using the prior art foils. The present invention also allows the stylist to use foils of any useful width, such as along a part line extending over half a head of hair with a single foil. Even very short hair, previously difficult or impossible to color or treat using the prior art, can be easily processed using the current invention.

Because of the decreased time required for the application of color using the present method, timing consideration of individual foils is greatly reduced. Use of transparent windows in the foils, or making the foils out of transparent material, further relieves the problem of inconsistency in the color from one foil to the next.

According to one aspect of the invention, there is a hair foil for use in chemical hair treatment procedures, consisting of a sheet of foil material and at least one hair anchor strip applied to one edge of either side of the sheet. The edge may be a pinked edge, and the hair anchor strip may be aligned with the pinked leading edge. The hair anchoring strip may function on the underside of the foil to grip the hair on the scalp and hold the foil in place, or on the upper side as a hair holding restraint to grip selected strands of hair being laid on the foil for coloring. The sheet may be fabricated, treated, or selected to have an upper surface for application of chemicals and an underside surface for contacting the scalp.

According to another aspect of the invention, the hair foil may have a push flap or other structure on the upper or lower surface of the sheet, oriented parallel to and proximate the leading edge, the flap being folded down and away from the leading edge so as to form a slot under the flap within which a tool may be inserted for urging the foil forward.

At least a portion of the upper surface of the sheet may be provided as or made tacky so that strands of hair are easily adhered to it. The sheet of foil may be configured with shoulder cut outs on each end of the leading edge, so that a portion of the sheet somewhat removed from the leading edge is wider than the leading edge itself.

According to yet another aspect of the invention, the hair holding or anchor strip whether functioning as an anchor on the bottom of the foil for engagement in the hair on the scalp or as a hair holding restraint on top of the foil for selected strands, may consist of one component of a hook and loop fabric fastener system, providing an important resistant to simple lifting of the foil or appliance in addition to resistance to lateral displacement.

The term "foil" as used throughout is meant to be interpreted broadly, and includes any sheet, film, foil, web, layer or substrate or the like that might be used to separate or partition the woven or selected hairs for treatment from the remaining hair and scalp.

According, there is a further aspect of the invention; the foil or film material or paper stock or other materials from which the foils of the invention are fabricated, may be a laminate, such as of paper and foil or other materials, that provides a chemically resistant moisture barrier for the scalp, and a receptive and suitable upper surface for conducting the chemical hair treatment process. The laminate may further function as a heat barrier, retaining the heat of the chemical process within a folded foil.

According to still another aspect of the invention, a hair appliance or tool or component of a foil system for use in restraining a section of hair to a desired place on the scalp consists of a base plate, whether flexible or rigid, whether elongate or not, the underside of which is at least partially configured with one component of a hook and loop fastener system. The edge of the appliance may have a pinked or zigzag design to facilitate picking of select strands of hair from beneath the appliance. The appliance may incorporate a top side hair clip or other additional hair retention device of any style by which an additional amount of hair or individual hair strands may be selectively attached to the appliance. The appliance may incorporate means, such as a clip, slot, or flat spot for adhesive attachment, for attaching a sheet of hair foil material to the appliance. The appliance or tool may be configured and function as a leading edge component of a foil system, used and attached to the scalp in a similar manner to the foils of the invention.

Another aspect of the invention extends to a method for making hair foils, including the steps of: using a continuous web of foil material with a width of at least twice the length of the sheet of a finished hair foil; applying a continuous strip of hair anchoring material to at least one side of the web at about the center of the web, splitting the web at about the center into two parts, and cutting each part into individual foils.

Yet another aspect extends to a method for making hair foils with push flaps for use in chemical hair treatment procedures, consisting of the steps of: using a continuous web of foil material with a width of at least twice the length of the sheet of a finished hair foil, where the web has an underside intended for placement against the scalp and an upper side intended for application of chemicals; folding a set of four adjacent fold lines into the center of the web with the first fold turning back on the upper side, and the second fold turning back on the underside, the third fold turning back on the underside, and the fourth fold turning back on the upper side so as to place the first and fourth fold lines between the second and third fold lines so that the second and third fold lines define what will be the push flaps.

There is then applied a continuous strip of hair anchoring material to the underside of the web so as to cover both first and forth fold lines, thus securing the joint from which the flap extends. Then the web is split between said first and fourth fold lines into two parts so as to split the continuous strip of hair anchoring material; and cut each part into individual hair foils. The splitting may be done as a pinking split, as with a rotary cutting wheel with a zigzag cutting edge, so as to yield a pinked edge on each of the two parts of the foil web.

Other goals, advantages and aspects of the invention will be apparent to those skilled in the art from the figures, description, and claims that follow.

BRIEF DESCRIPTION OF DRAWINGS:

FIGS. 1a–1e depict a sequence in which FIG. 1a depicts the process of segmenting a head of hair to create a part line by using a hair restraint appliance of the invention, and placing a foil of the invention opposite the hair restraint appliance at the part line.

FIG. 1b depicts the process of weaving or picking hair along the part line from under the foil, through an underside scalp anchor component of the foil, and placing it on the upper surface of the foil.

FIG. 1c depicts the use of a pick under a leading edge foil flap to urge the foil towards the scalp and part line, for final positioning of the foil and full engagement of the selected hairs into the leading edge slots.

FIG. 1d depicts the application by brush of hair treatment formula to the selected hair disposed on the foil.

FIG. 1e depicts the foil having been folded up over and enclosing the hair to create a processing chamber.

FIG. 4a illustrates a first variation of the upper surface of a preferred embodiment hair foil of the invention, with a pinked edge, push flap, and a continuous hair holding strip slightly displaced from the pinked edge.

FIG. 4b illustrates a second variation of the upper surface of a preferred embodiment hair foil, with a pinked edge, push flap, and a pattern of hair holding elements.

FIG. 4c illustrates a third variation of the upper surface of a preferred embodiment hair foil with a pinked edge, push flap, and a continuous hair holding strip applied adjacent to the pinked edge.

FIG. 5a illustrates a first variation of the lower surface of a preferred embodiment hair foil of the invention, with a pinked edge, a first continuous hair holding strip disposed and trimmed to match the pinked edge, and a second continuous hair holding strip slightly displaced from the first strip.

FIG. 5b illustrates a second variation of the lower surface of a preferred embodiment hair foil, with a pinked edge, and a rigid or semi-rigid pattern of hair holding elements in the form of a set of comb-like teeth angled back from the leading edge so as to allow the foil to be placed on the scalp by a smooth engagement of the teeth into the subject's hair.

FIG. 5c illustrates a third variation of the lower surface of a preferred embodiment hair foil with a pinked edge, and a pattern of hair holding elements disposed close to the pinked edge.

FIGS. 6a and 6b depict the top side view and edge of a foil with a pinked edge, hair holding strip on the top side adjacent to the pinked edge, hair treatment reservoir on the top side, and two spaced apart hair holding strips on the bottom side.

FIGS. 7a, 7b and 7c are top view illustrations of three preferred slot terminations in the pinked edge of preferred embodiment foils, a narrow slit, V slit, and slit necked hole.

FIGS. 8a and 8b is an edge view depicting the head to head assembly process for fabricating preferred embodiment foils, before and after separation.

FIG. 9 is a perspective view of a preferred embodiment hair appliance with a pinked straight edge, and a hair holding hooked surface on both the top and bottom sides.

FIG. 10 is a perspective view of another preferred embodiment hair appliance, a leading edge component of a foil system, with a pinked edge, hair holding hooked surface on the bottom side and a folding hair clip on the top side.

FIG. 11 is a perspective view of a continuous length of leading edge material having a pinked edge, a hair holding hooked bottom surface and a tacky topside surface; which can be produced and distributed in bulk and cut to any desired length at the time and place of use.

DESCRIPTION OF THE PREFERRED EMBODIMENT

The invention is susceptible of many embodiments of apparatus and methodology. U.S. parent application Ser. No. 10/329815, filed on Dec. 23, 2002, by the same Applicant, is incorporated by reference, including such prior art as is cited. The preferred embodiments explained herein are illustrative and not limiting of the scope of the invention.

Figure 1A:
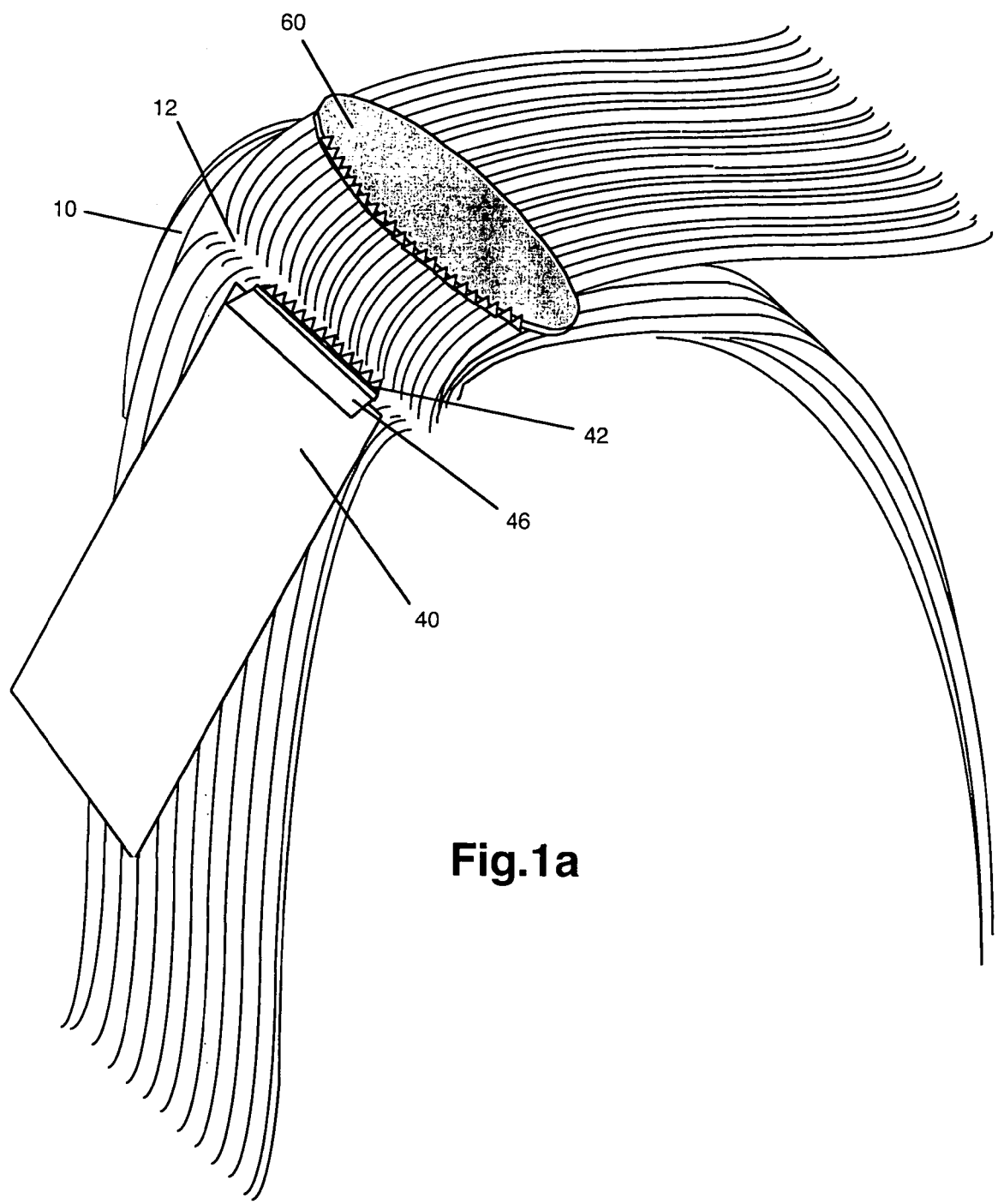

Referring to FIGS. 1a–1e, preferred embodiments of the invention are illustrated in the form of a sequence of process steps. FIG. 1a depicts the process of segmenting a head of hair 10 to create a part line 12 by using a hair restraint appliance 60 of the invention to hold one side of the parted hair in place. The stylist can then place a foil 40 of the invention, configured in this embodiment with its pinked leading edge 42 and push flap 46, onto the hair at the part line opposite the hair restraint appliance 60.

Figure 1B:
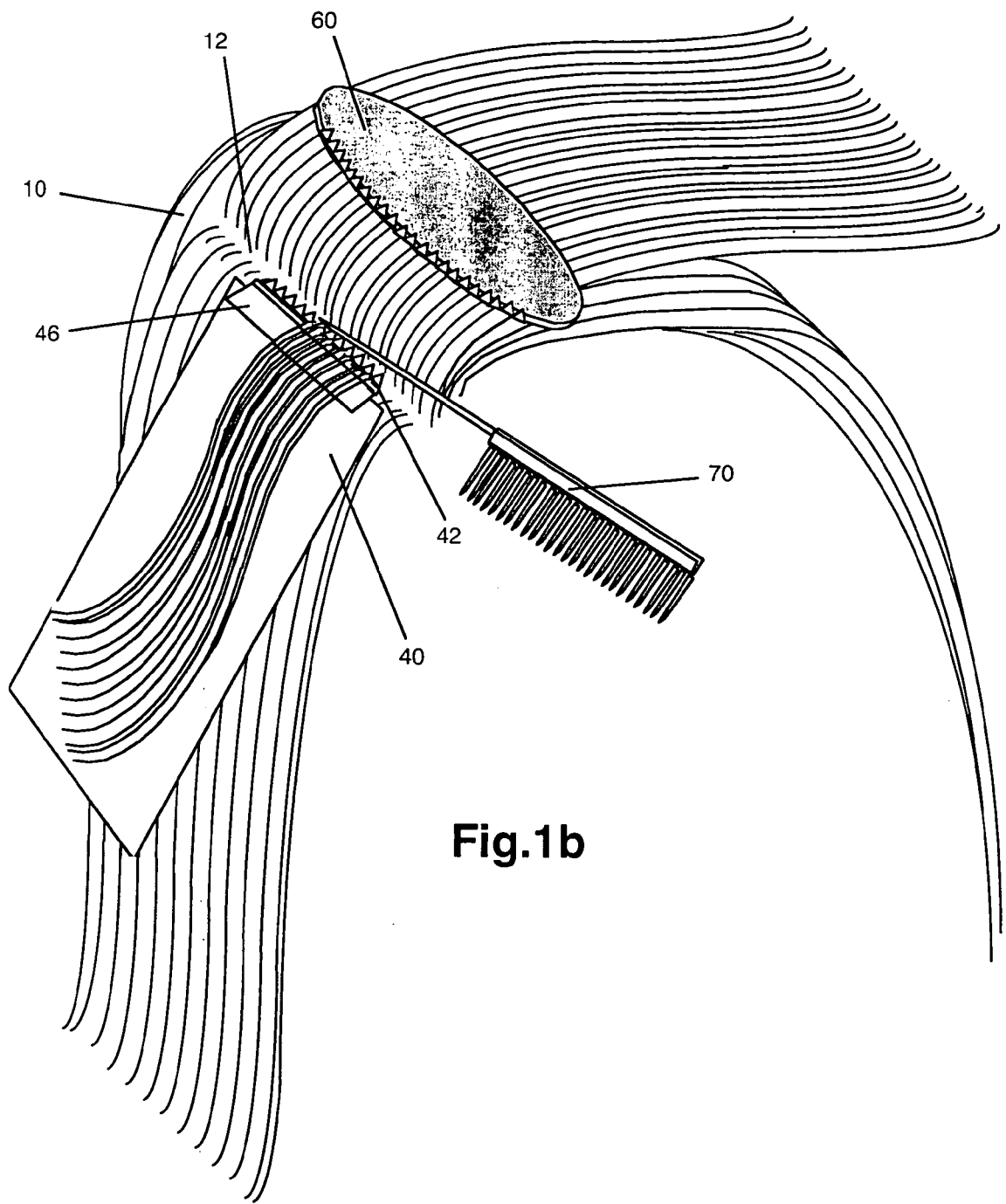

FIG. 1b depicts a further point in the process, showing the weaving or picking of selected hairs with the handle of comb 70 along part line 12, from under foil 40 and through its bottom side hair anchor component (not shown in this figure) of the foil. The selected hairs are being drawn down into the slots of leading edge 42 and laid across push flap 46 and down on the upper surface of foil 40.

Figure 1C:
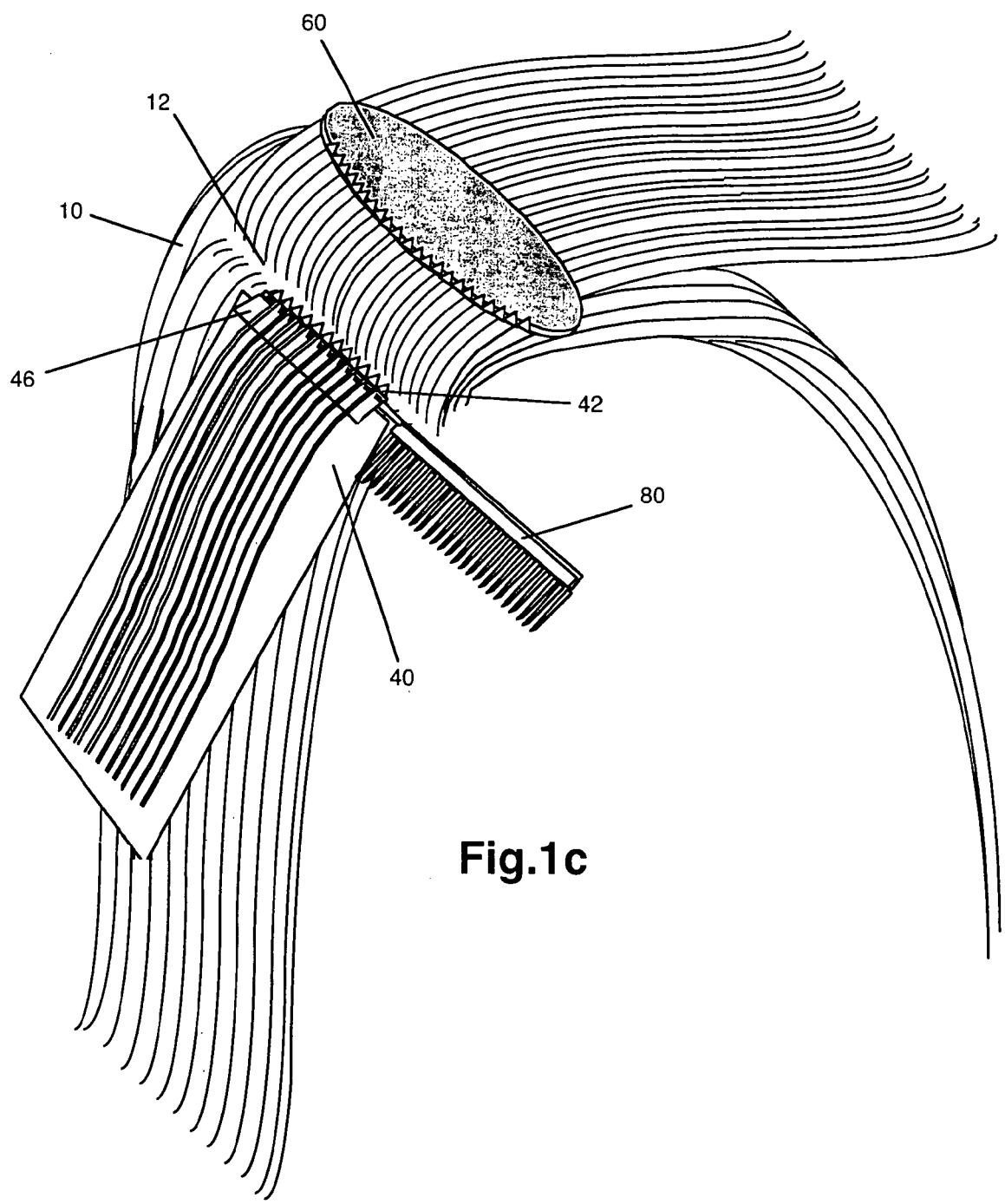

FIG. 1c depicts a yet further point in the process, where the weaving and placement of hair on foil 40 is complete, and the handle of comb 70 has been positioned behind flap 46 and used to urge the foil towards the scalp and part line for final positioning of the foil and full engagement of the selected hairs into the slots of leading edge 42.

Figure 1D:
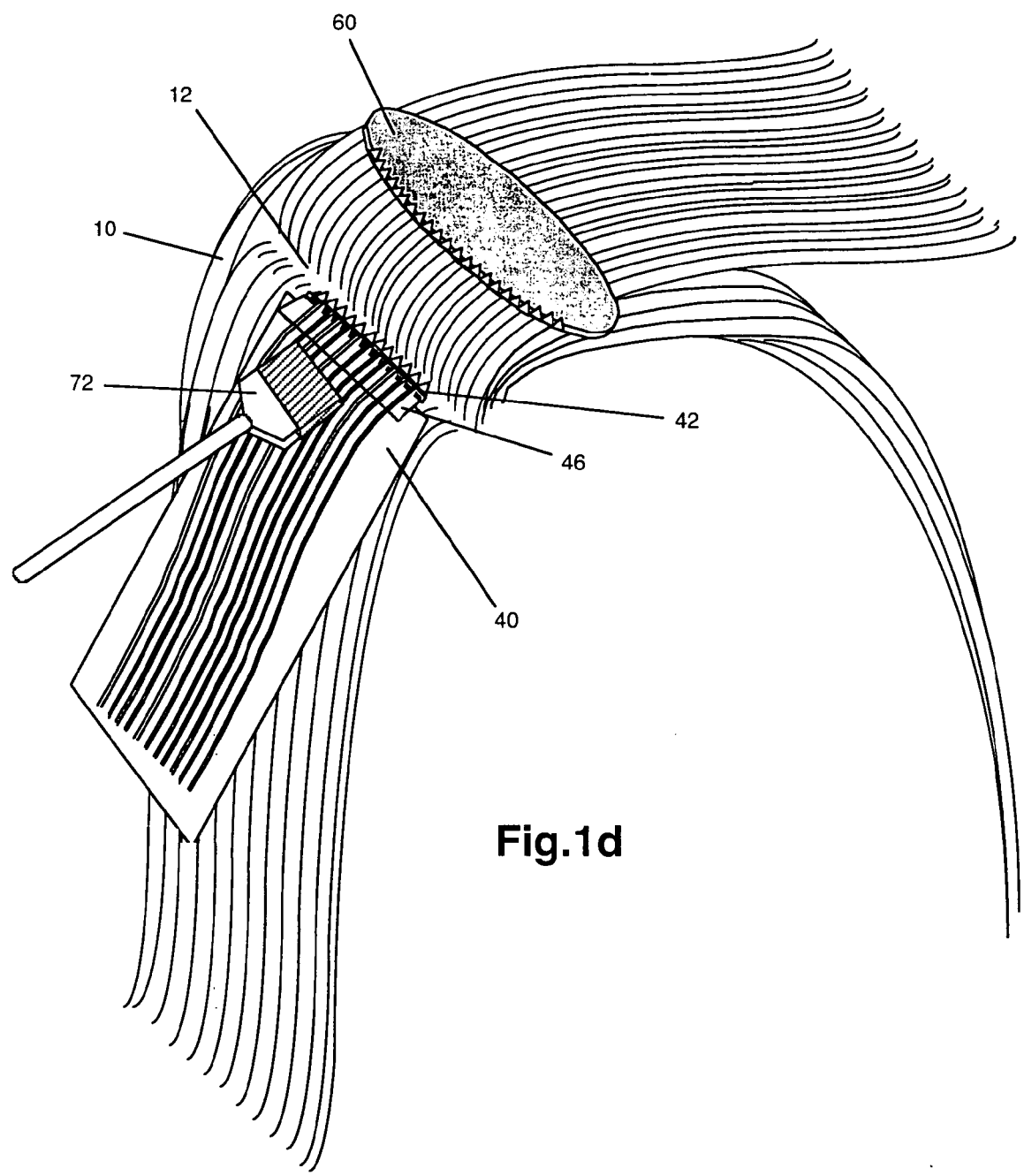

FIG. 1d depicts a still yet further point in the process, the application with brush 72 of the desired hair treatment formula to the selected hair disposed on foil 40.

Figure 1E:
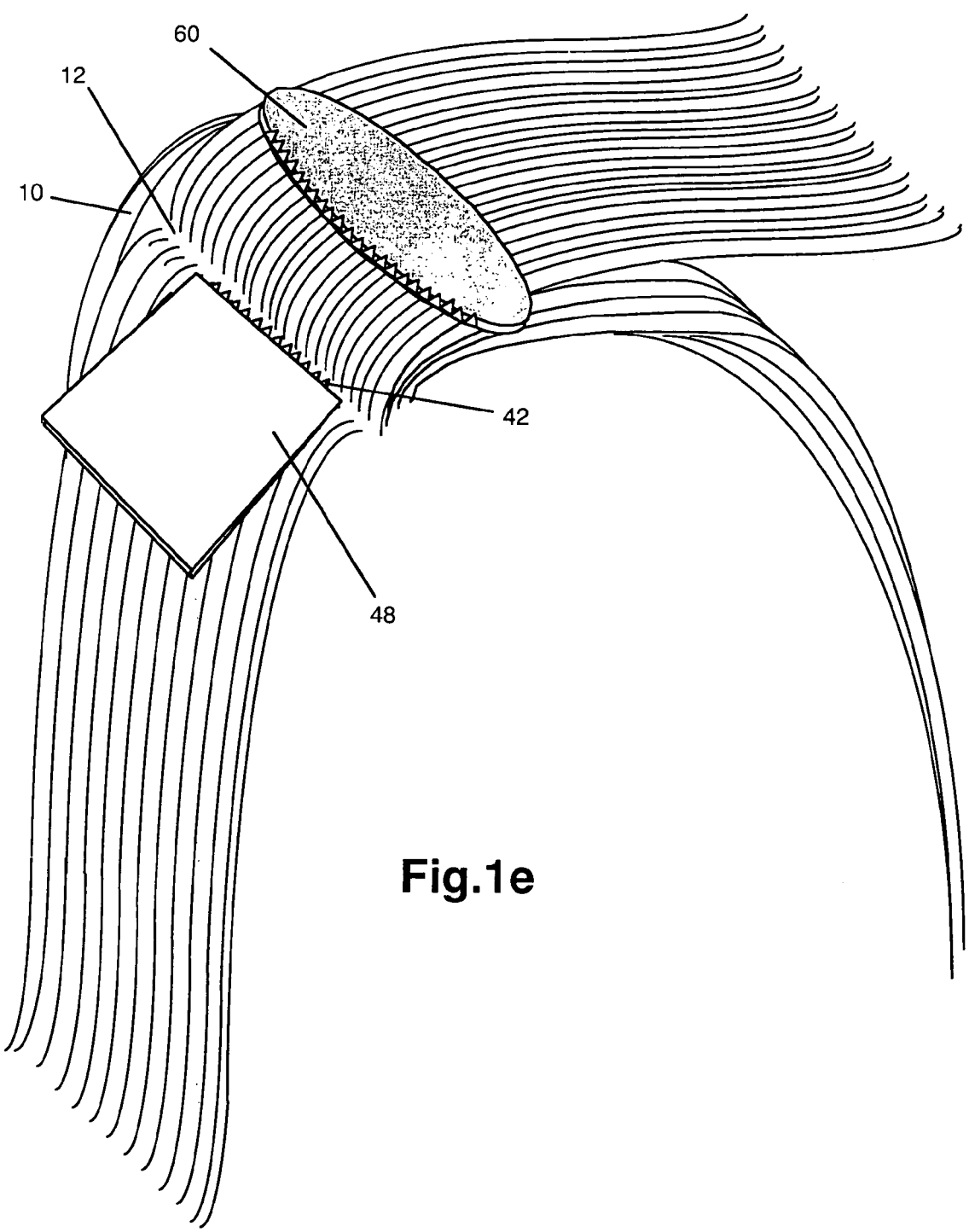

FIG. 1e depicts an even yet further point in the process, foil 40 having been folded over on itself, assuring its grip on the selected hairs, and enclosing the selected hairs to create a processing chamber within which the hair chemicals perform their function.

Figure 2:
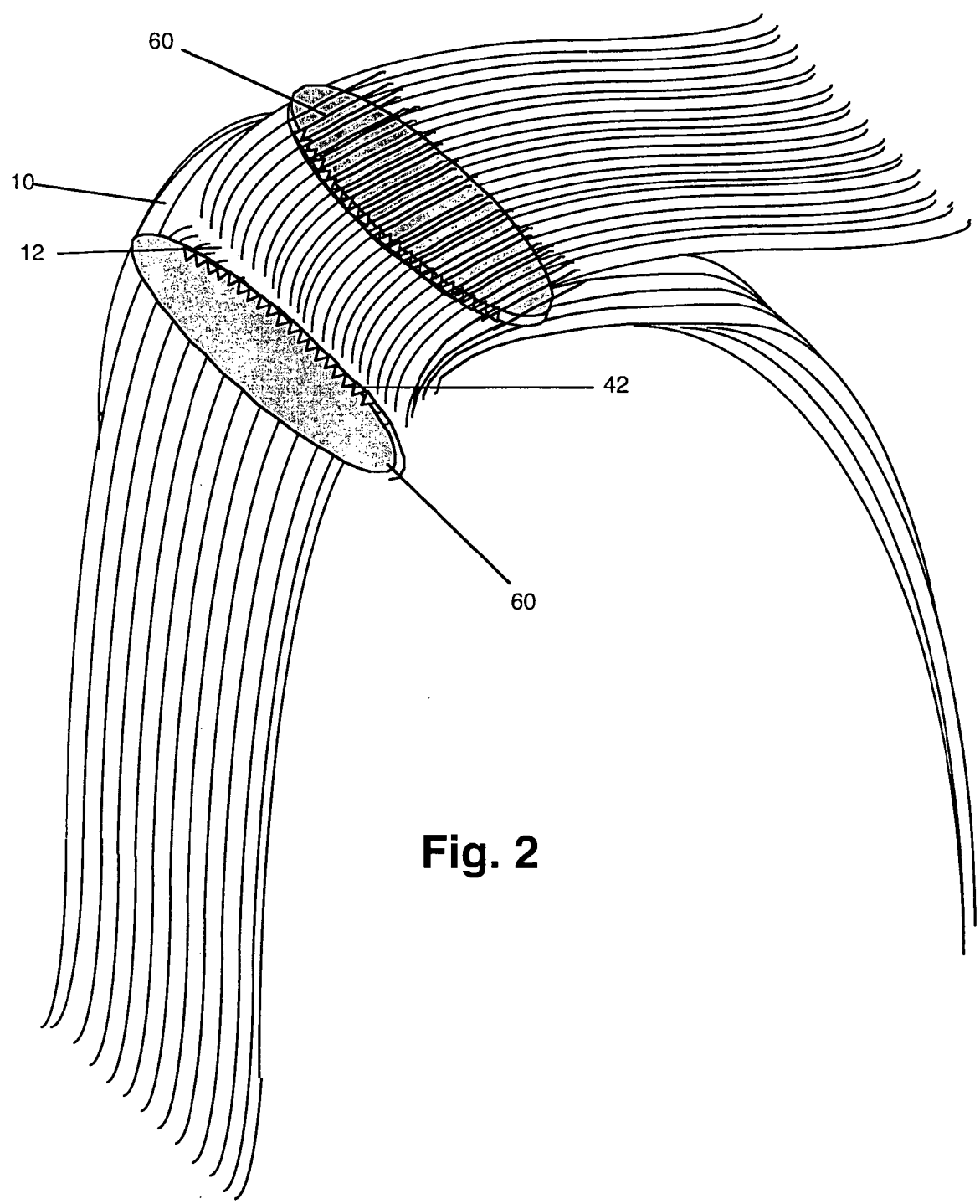
FIG. 2 depicts the use of two hair restraint appliances of the invention; one used to segment the hair and define a part line in a head of hair, the other placed opposite the first appliance at the part line to function as a hair selection tool.

FIG. 2 illustrates the use of two hair restraint appliance 60s of the invention, each having a pinked leading edge 42 and hair holding elements on each surface, as is described further below. One appliance 60 is used to segment hair 10 and define a part line 12. The other appliance 60 is placed opposite the first appliance at the part line to function as a hair selection tool. As is illustrated, the selected hair has been laid up over the upper appliance 60, being held in place by the upper surface hair holding element.

Figure 3:
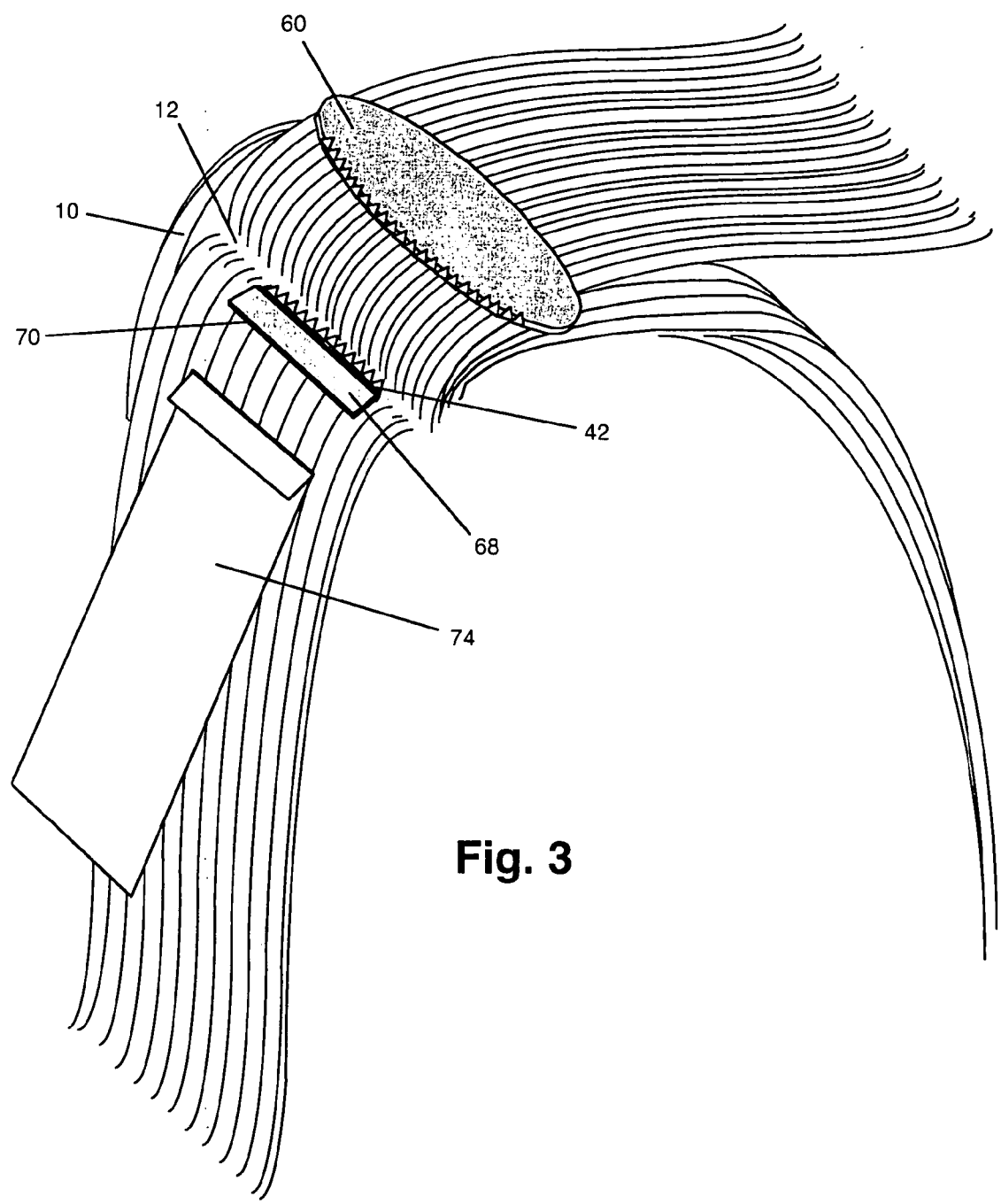
FIG. 3 depicts the use of a hair restraint appliance of the invention to segment the hair and define a part line in a head of hair, and a leading edge appliance component of a multi-part foil system of the invention.

Referring now to FIG. 3, there is illustrated the use of a hair restraint appliance 60 to segment hair 10 and define part line 12. A leading edge appliance 70, part of a multi-part foil system embodiment of the invention having a pinked leading edge 42 and a tacky upper surface 68 to which foil blank 74 may be attached, has been placed in the hair at part line 12 opposite appliance 60. Foil blank 74 may be attached to the tacky upper surface 68 of appliance 70 prior to placement of 70 on the scalp, or as shown here, after placement of appliance 70 on the scalp.

FIGS. 4a through 4c illustrate three preferred embodiment upper surface views of a foil of the invention. Foil 40 of FIG. 4a is configured with a pinked leading edge 42. Notice that the width of foil 40 is noticeably wider than leading edge 42, providing a larger area of protection to the scalp from the chemicals of the process than otherwise. There is a leading edge flap 46, the upper surface of which is configured with a hair holding strip 45a consisting of a hooked surface similar to the hook component of a hook and loop material fastening system.

FIG. 4b illustrates a second variation of the upper surface of foil 40, having the same pinked edge 42, and push flap 46. However, the hair holding strip 45a of FIG. 4a has been replaced with a pattern of smaller hair holding elements 45b, which may be a hooked surface as in FIG. 45a, or a tacky surface element to which selected hairs are easily stuck and released.

FIG. 4c illustrates a third variation of the upper surface of foil 40 having the same pinked edge 42 and push flap 46, but configured with a different hair holding strip, a tacky surface hair holding strip 45c, to which selected hairs are easily stuck and released, applied adjacent to the pinked edge.

Referring now to FIGS. 5a through 5c, there are illustrated three preferred embodiment bottom side views of foil 40. FIG. 5a illustrates a first variation of the lower surface of a foil 40, with a non-permeable underside layer 48, a pinked edge 42, a first continuous hair holding strip 44a disposed and trimmed to match the pinked leading edge 42, and a second continuous hair holding strip 44a slightly displaced from the first strip and extending in length the full width of foil 40. Hair holding strips 44a may consist of a hooked surface, or a tacky or adhesive surface, either of which is easily engaged, retains the foil in position during use, and is easily disengaged from the hair when finished.

FIG. 5b illustrates a second variation of the lower surface of a foil 40, having the same non-permeable underside layer 48, pinked edge 42; but having a rigid or semi-rigid pattern of elongate hair holding elements in the form of a hair holding comb 44b of comb-like teeth angled back from the leading edge so as to allow the foil to be placed on the scalp by a smooth drawing down into or sliding engagement of the teeth into the subject's hair, with the teeth being held generally aligned with the hair and perpendicular to the part line during the act of engagement. The profile and spacing of the teeth of comb 44b may vary considerably, so long as the basic functionality of easy engagement, retention of the foil in place during use, and disengagement, is assured.

FIG. 5c illustrates a third variation of the lower surface of a foil 40, having the same non-permeable underside layer 48, pinked edge 42; but having a pattern of hair holding elements 44c disposed close to the pinked edge and having the same basic functionality as the hair holding structures of FIGS. 5a and 5b.

Referring now to FIGS. 6a and 6b, there is illustrated by top side plan view and edge view a preferred embodiment foil 40 with a pinked edge 42, top side push flap 46, hair holding strip 45 on the top side adjacent to the pinked edge, shoulders 47 on either side of pinked edge 42, a non-permeable bottom side 48, and two spaced apart hair holding strips 44 on the bottom side of the foil, and in particular a hair treatment reservoir 41, recessed in the foil so as to be accessible from the top side of the foil, but projecting in profile or thickness, in so far as is necessary, out of the underside of the foil, as is visible in FIG. 6b. The bulge or shoulder of reservoir 41 does not interrupt the otherwise smooth surface aspect of the top side of the foil.

The reservoir 41 provides for a pre-packaged amount of chemical hair treatment that may or may not require water or some other activating ingredient to be added in order to make it effective for hair treatment. The reservoir may be opened any means such as by use of a tear strip or peel off surface covering or by piercing the reservoir envelope with a tool.

Shoulders 47 extend the width of the foil beyond the width of pinked edge 42, providing extended surface area for placement of fingers when placing the foil and for extended coverage and protection to the scalp and underlying hair while applying chemicals and a larger working surface upon which to lay down the selected hair strands and apply the chemicals. Actual sizes can vary, but some useful embodiments have leading edges in the range of two to four inches long with foil widths ½ to ¾ inches wider on each side. While the preferred embodiment illustrates square cut shoulders, other embodiments may employ any variation providing additional width and surface area.

The upper strip 44 extends just the length of pinked edge 42, while the lower hair holding strip 44 extends the full width of the foil so as to extend its anchoring function over the full width of the foil.

Referring now to FIGS. 7a, 7b and 7c, there are illustrated by close up, top side views at the pinked edge 42 of a foil 40, three preferred slot terminations in the pinked edge; a narrow slit 43, a V slit 43b, and slit necked hole 43c. Any of these termination structures, and other variations of the nip at the bottom of the pinked trough provide for a fuller encasement or closure around the roots of the few weaved hair strands in each trough. This assures better containment of the chemical hair treatment to the top side of the foil and away from the remaining hair and scalp of the subject.

FIG. 8a is a sections or edge view illustrating the head to head continuous length assembly process for fabricating a continuous web of head to head preferred embodiment foil material. Suitable sheet material is folded at points 57 to provide pockets 59 below flaps 46, symmetrically about center line 69. Continuous hair holding strips 44 are adhered to the bottom side. The resulting web of head to head foil stock can then be chopped to width and then slit or pinked to divide it into to finished foils; or slit or pinked to divide the web into two webs each having a pinked edge 42, the left hand half of the web of FIG. 8a being illustrated by the section or edge view of FIG. 8b. The web of FIG. 8b is then subsequently chopped or cut to the desired foil width.

Referring now to FIG. 9, there is illustrated in a perspective view a preferred embodiment hair appliance 60, with a pinked straight edge 42, and a hair holding surface 62 on each of the top and bottom sides. The appliance is essentially reversible; either surface may be placed or engaged in the hair on the scalp, and additional selected hairs may be placed on the top for restraint in any way useful to the stylist. One or the other or both hair holding surfaces 62 may be a hooked surface.

It should be noted here that the appliance 60 and other embodiments of the invention provide benefits well beyond the needs and interests of hair stylists. Medical personnel and others who are required to examine or work on or otherwise treat a person's scalp or hair will appreciate a quickly applied device to help hold a part line, with a receptive top surface available for holding yet more hair, whether placed one or a few strands at a time.

Referring now to FIG. 10, there is illustrated in a perspective view a preferred embodiment hair appliance 64, having a pinked edge 42, a hair holding hooked surface (not shown) on the bottom side and a folding hair clip 66 on the top side. The device is placed on the hair and scalp in the same manner as appliance 60 of FIG. 9; however the hair clip 66 endows appliance 64 with a greater top side hair holding capacity, albeit with the need to open and close the clip for placement and retention.

FIG. 11 is a perspective view of a continuous length of leading edge component 68 of a preferred embodiment foil system, characterized by a pinked edge 42, a hair holding hooked bottom surface (not shown) and a tacky topside surface 61. The continuous length component 68 is produced and can be distributed in bulk and cut to any desired length at the time and place of use. Tacky surface 61 provides for the ready attachment of a foil blank of any suitable size and characteristics.

It will be appreciated that a foil of the invention may be configured of any sheet material suitable to protecting the scalp from the process chemicals used in the hair treatment. A minimal embodiment of a foil of the invention identifies a leading edge of the foil and incorporates a means for attaching the leading edge of the foil to the scalp adjacent a part line in the hair, and a means for securing or adhering selected strands of hair to the upper surface of the foil. Such means for attaching the foil to the scalp may be as simple as a top side or underside line or strip of adhesive such as a strip of double sticky-back tape, or an adhesive strip that can be exposed by removing a covering strip or flap. Such means for securing the hair strands to the upper surface of the foil may be as simple as a full or partial surface layer of a tacky finish or adhesive layer sprayed on or otherwise provided for in the manufacturing process, or a layer of a chemical mixture intended for hair treatment that doubles as an adhesive for holding the hair on the foil and/or holding the folded faces of the foil together.

The scalp attachment or hair holding or anchoring mechanism, which as described above may be configured on either the top or bottom surface of the foil near or adjacent to the leading edge, and the hair strand securing or hair holding feature on the topside of the foil, can both be accomplished by more structural means. For example, a simple pipe cleaner bristling over its length with small thistles that will engage strands of hair can be used on the underside surface to engage the hair of the scalp or on the upper surface to engage the selected strands of hair. In either case, it provides a useful degree of hair gripping power for the hair foil. As another example of an attachment mechanism, a comb-like structure of elongate teeth on the underside surface can be sufficiently engaged in the hair of the scalp to hold the foil in place.

A preferred embodiment hair foil of the invention utilizes at least one strip or a pattern of smaller spots of the hook component of a conventional hook and loop fabric fastener system or equivalent or similar structure. This is referred to in this specification as a hooked surface. It has been found that the hook material with its extended pattern of small plastic barbs or hooks projecting from a base surface, is particularly advantageous in that it is easily emplaced and entangled in the hair along the part line for retaining placement of the foil or appliance in position on the scalp. It is later easily removed, and also individual hair strands can be weaved or withdrawn laterally through the barbs of the hook component material from under the foil edge with a pick or tool, for lifting and processing. Variations on the commonly available hook and loop materials directed specifically to the hair gripping objective of the invention, however formed and of any suitable material, are within the scope of the invention.

Likewise, a strip or patch of the same or similar material can optionally be applied to or incorporated into the upper surface of the foil as a hair strand holding strip, with or without a tacky surface or other adhesive layer, to assist in handling the picked hair strands for treatment. Further enhancements of the basic concept are incorporated into preferred embodiments, as is further described below.

As explained above, in the prior art of hair foils and hair processing, a few strands of hair are "woven", that is to say, hairs in a certain region of the head are selected and pulled out and collected together, held aside while a foil is positioned, and then laid onto the foil for chemical treatment. The foil is then folded, typically twice, to secure its grip on the strands of hair, hence securing the foil by those strands of hair in position on the scalp.

As previously noted, major advantages of the improved foil of the invention are that it clings to the hair on the head of the subject being treated without the stylist having to hold the foil in place, and that it permits picking of selected strands of hair and pulling them from beneath the emplaced foil for placement on the foil surface for treatment.

Referring to FIGS. 1, 3, 4, 5, 6, and 8, a preferred embodiment foil of the invention includes a substantially rectangular sheet of thin, pliable, chemically resistant material. At least the lower surface of the sheet incorporates a non-permeable moisture barrier, and may function in part as a heat barrier, while the upper surface may be slightly moisture absorbent so as to retain the liquid or paste chemicals applied to the foil surface and hair of the subject, thereby preventing runoff of the chemicals. The upper surface may be slightly tacky so as to hold hair strands in place and/or to provide for folding over and adhering the trailing end to enclose the hair strands being colored. The color of the upper surface may be selected to provide a useful degree of contrast to the hair colors being applied.

The preferred size of a basic foil is approximately four inches in width, and double the width in length, in this example about eight inches in length, so that the foil can be conveniently folded over on itself during the process, placing the trailing or opposite edge in proximity to the top edge when first folded. As in the prior art practice, the fold line end of the foil may be then folded again to the leading edge and secured by conventional means.

In one embodiment, the top edge of the sheet, which is sometimes referred to herein as the leading edge or the part line edge, has a "pinked", or zigzag tooth pattern, which creates channels along the edge within which hair strands may be uniformly picked or selected, distributed into the appropriate channel or V slot, and laid down across the surface of the foil. The pinked edge provides an ergonomic aid to the stylist in working incrementally and uniformly along the leading edge of the foil and selecting a uniform distribution of strands along the part line, and pulling them from beneath the foil, in contrast to the prior art method of pre-selecting the desired strands before placing the foil. One might characterize the distinction between the method of the present invention and the prior art methodology as "Placing (the foil) and then picking (the desired strands from under the foil of the invention)" versus "picking (the desired strands) and then placing (the prior art foil)."

A pinked cut or edge design has a commonly understood zigzag pattern in the plane of the foil, and is preferred for its simple geometry with pointy ends that better engage and divide hair when urged forward and the visible slots through which strands can be selected. However other edge designs providing a uniformly incremental tongue and slot pattern, such as a square wave or sine wave design, are all within the scope of the invention. A further refinement of some embodiments, as illustrated in FIGS. 7a, 7b and 7c, provides a small, narrow, terminal slot feature at the bottom of each channel into which the selected hair strands are pulled and tend to lock as they are pushed in after placement as the foil is urged forward towards the part line by the use of the pick or other tool. Upon wetting of the strands with the process chemicals, a swelling takes place that tends to enhance the holding power of this terminal slot on the strands under treatment. While an edge pattern as described is desirable, the invention does encompass embodiments with merely a straight leading edge.

Other embodiments of the foils of the invention provide for a downward projecting pattern of teeth at and under the leading edge of the foil instead of or in addition to the pinked edge pattern, that project into the parted hair under the foil and secure the foil in place, and yet through which selected strands can be pulled from under the foil, for processing.

Referring now to FIG. 3, the lower or scalp-side surface along the leading edge of a preferred embodiment foil contains a hair holding anchor strip which holds the foil in position on the scalp by means of a hooked surface, comb-like teeth, adhesive, gel spots, or other hair-gripping, sticking, or grasping features of the material. As illustrated in FIGS. 5, 6 and 8, the hair gripping attachment anchor strip may be formed of an elongated, substantially rectangular piece of material, which is then pinked to match the pinked edge of the foil. The hair holding anchor strip further provides some rigidity to the top edge of the foil, so that it does not curl or collapse during placement or use. The anchor is preferably bonded to the foil by adhesive or heat fusion. In preferred embodiments, the foil edge and the anchor strip are pre-assembled and then pinked in the same operation.

It should be noted here that the hair holding anchors of the foil, particularly when comprising the hook surface described, performs to both grip the scalp, and permit hair strands to be selected and drawn from underneath the foil.

Referring again to FIGS. 4, 6 and 9, the upper surface of a foil may also contain a hair holding strip, typically attached to the foil in proximity to the pinked edge, but in other embodiments displaced somewhat, such as about one-quarter inch, from the pinked top edge. This element of the invention is preferably formed from an elongated, substantially rectangular piece of material, which may be pinked along one or both edges. Referring particularly to FIGS. 4b, alternative configurations providing substantially full width effectiveness, such as a series of smaller hair holding structures, for example a stripe pattern of small squares, spots, patches, or circular sections, or small strip sections diagonally laid, however arranged, are within the scope of the invention. This is somewhat analogous to the underside hair holding pattern illustrated in FIG. 5c.

The top side hair holding strip or strips help to keep the hair strands to be colored in place on the upper surface of the foil, and further help to retain the foil in position on the scalp. The hair holding strip may be made of the same material as the hooked surface described elsewhere. A preferred design or material for the hooked surface, wherever employed or however integrated in the invention, is similar to Velcro® brand hook and loop material, or variations thereon. No claim is made to the trademark Velcro®. In preferred embodiments, the hooked surface is bonded to the foil by adhesive, although other means of attachment or even integral molded hooked surfaces, are within the scope of the invention.

The embodiment of FIG. 6 contains reservoir 41 which may be a strip or pad of a spongy foam material of an interconnecting cellular orientation, which is attached to the upper surface of the foil by an adhesive or otherwise incorporated into the foil structure. It may be an envelope that functions as a fluid or paste reservoir for the hair treatment material. The reservoir may be made of any number of materials, including natural sponge, or synthetic sponge materials, such as cellulose. It may have a protective sheet or be otherwise sealed until needed; and be openable by a tear strip or tool, or simply require the addition of a wetting agent to release it and make it flow. It is particularly applicable to embodiments of the foil provided for home use, while professional stylists may prefer to select, prepare and apply their own chemicals or color treatment.

In the embodiment of FIGS. 6a and 6b, the application reservoir is loaded with the coloring chemicals in either paste form, or as a dried liquid, which must be moistened prior to use. A brush is used to transfer the chemicals from the sponge to the hair strands.

As seen in the top plan view of FIG. 6, the application reservoir 41 extends across the width of the foil, and is about an inch in width. In the side elevation view of FIG. 6b, the application reservoir thickness is equal to, or slightly greater than that of the hair holding strip 45. It may not be significantly greater, or it may interfere with the function of the hair holding strip. However, the reservoir is not otherwise limited to the size or placement shown. For example, it may be a dry or tacky thin film coating uniformly applied to the surface of the material from which the foil is cut, to be later activated by application of water or other wetting agent when the foil is used. It may be a simple blister or bubble type reservoir, opened by a tear strip or other means of perforation.

Referring again to FIGS. 4, 5 and 6, a preferred embodiment foil consists of a non-permeable or foil underside layer and a paper upper side layer. All or a portion of the top side layer may be treated with a tacky adhesive or gel to which hair strands will adhere, and by which the trailing end of the foil can be folded over and adhered to the leading edge end of the foil, enclosing the hair strands as described above. A portion of the foil, particularly the trailing end half, may incorporate a window of non-permeable material which when folded over as described, permits visual inspection of the enclosed hair strands for chemical and color progression. Other embodiments may be oriented with the sealing section or sections folding over from one or both sides of the foil to enclose the colored strands, rather than from the trailing end as described. Other embodiments may have multiple sealing flaps extending on all three available sides of the foil for abutting or overlapping enclosure of the selected hair strands.

Referring in particular to FIGS. 1, 6, and 8, these embodiments are configured with a push flap 46, defining a slot 59 (FIG. 8*b*) that aids in placing and using the foil. When strands of hair have been picked and laid over the push flap and onto the foil as described, the several strands hold push flap 46 securely against the foil so that pushing a tool into slot 59 for realigning the foil on the scalp cannot open the flap.

Referring again to FIGS. 8*a* and 8*b*, a preferred means of fabricating foils of the invention in web form is to provide sheet foil material in a width approximately twice the length of a desired foil, folded along the center line as shown in FIG. 8*a* so as to represent two foils with abutting at their leading edges. Note that respective fold lines 57 of the abutting foils are spaced apart about the width of the pinking cut. After strips 44 are applied and the assembly is compressed for adhesion, the single web of two foil widths is cut into two webs of one foil width, preferably by a pinking cut through centerline 69. Referring to FIG. 8*b*, the pinked hair holding strip 44 on each resulting web of foil extends across fold line 57 to the extreme tips of the pinked edge, thus assuring the integrity of push flap 46 and pinked edge 42 when applying pressure with a push tool of any sort within slot 59.

Other foil designs and other means for fabricating the foils are within the scope of the invention. The foils can be hand made in a stylist's shop from commonly available materials, although it may be tedious and time consuming. Foils can be fabricated in a roll or sheet with a common leading edge, and cut off or torn at perforations as needed. A strip or roll of the leading edge section can be provided, to which foil blanks of the desired size are applied as needed. Manual or automated foil fabrication can include one or multiple flaps or folds incorporated into the upper or lower surface to aid in placement, to cover or shield tools used in placement, to cover adhesive sections until needed, and so on.

Foils may be designed and fabricated to be reusable once or several times, although preferred embodiments are considered disposable after a first use. Alternatively, a foil "head" or leading edge section may be fabricated to be reusable, to which are attached disposable foil blanks for each new use.

Referring again to FIGS. 9–11, in addition to the improved foils and appliances of the invention, other related tools and appliances are herein disclosed. For example, there may be a temporary hair restraint tool consisting of a base plate in the shape of a barrette, with its underside fully or partially configured with anchor strip material, preferably the hooked surface variety as described above. The base plate of the hair restraint may be flexible or semi-rigid or rigid, curved or flat, and range in size from an inch or less to four inches or more in length. One edge of the base plate may be configured with a straight or curved line segment of pinked edge, for the same reasons ascribed to the pinked, leading edge of the foils and other appliances. The base plate may incorporate a large hair clip over its topside so that some hair can be selectively laid over and clipped to the hair restraint. The temporary hair restraint may be configured or adapted for attaching or receiving a foil blank and functioning in the manner of the foils of the invention. The foil blank may be simply adhered or clipped to the top or one edge of the base plate. As with the foils and other appliances of the invention, the tool may be placed first, and then strands of hair selected along the pinked edge and pulled from beneath the base plate of the tool through the anchor or hair holding strip and gathered for the desired purpose.

Another simple hair retaining tool of the invention is a flexible plastic pad of substantially oval shape, fabricated with a straight edge section along one long edge, with the straight edge section and at least a portion of the remaining edge having a pinked style edge detail. The underside is fabricated with an anchoring structure, preferably a hooked surface as described above. The tool is quickly and easily placed anywhere on the scalp to retain a section of hair, and just as easily removed, in the same manner as the foils of the invention. The pinked edge section provides the same "place and pick" capability as the foils and other appliances of the invention, enabling selected strands to be drawn from beneath the tool while it is in place. The pinked curved edge portion provides for a contoured effect in the selection of hair strands not normally considered with conventional straight edge foils.

It will be readily apparent that the tools and appliances of the invention can be used in conjunction with foils of the invention or with prior art foils to facilitate the application of various hair treatments.

Referring again to FIGS. 1*a*–1*e* generally, the differences in the methodology of hair processing with the foils and other tools of the invention as described above are dramatic, significantly impacting the professional stylist's productivity, as well as improving the quality and consistency of the results. These differences in operating technique will vary somewhat between individuals but will generally be readily appreciated to those skilled in the art from the description of the foils and tools provided above. They are here only briefly presented in the context of several of the foil embodiments described, for the benefit of the uninitiated.

The process starts by dividing the hair on the head into workable segments separated by part lines. One or more hair restraining tools or appliances of the invention may be employed in this respect. This simplifies the use of foils by dividing and holding sections of hair out of the way while a particular section is being worked on.

The foil is next attached to the hair in proximity to a part line using the attachment anchor strip on the lower surface of the foil to hold the foil in place on the subject's scalp. The zigzag design of the pinked edge is placed closely to one side of the part line so that the foil is securely in position with the leading edge close to the scalp.

The stylist, using a pick tool or pick attached to a comb, draws strands of hair from under the foil, through the anchor strip on the underside of the foil, and places it in the appropriate V slot of the pinked, zigzag edge pattern. Hair that is drawn from under the sheet will thus be "picked" along the entire leading edge of the foil, creating a uniform density of hair strands along the entire top edge of the foil. The density of hair strands thus "picked" will be substantially less than the subjects normal hair density, so that only a desired percentage of all available strands is disposed at the top of the foil to be colored.

The flexibility in choosing the density of strands to be treated, and to treat very short lengths of hair, is as enabled with the present invention, allows for the creation of many patterns of color and designs which were not practical using the methods, foils and tools of the prior art.

Next, the stylist presses the "picked" or selected strands of hair against the upper surface of the foil in a distributed or separated pattern. Referring back to the foil embodiments illustrated, particularly to FIG. 1*c*, the pick is now used to make a final adjustment of the foil by pushing the foil towards the scalp or hairline from within the slot beneath push fold 46, or from beneath the foil against the underside hair holding strip for embodiments not having the illustrated flap, so as to realign the foil to the hairline if any movement occurred through the picking and pressing process, and also to lock the selected hairs into the terminal slots of the embodiments illustrated in FIGS. 7a, 7b or 7c.

A liquid chemical hair processing mixture is then applied to the hair on the foil by means of a brush or sponge, being careful not to let the mixture contact any surrounding hair. The hair can be worked on the foil to insure a proper coating of the coloring chemicals. As was described above, in some embodiments the coloring chemicals are packaged with the foil, and exposed for use when the foil is applied.

After the chemicals are suitably applied to the strands, the foil is folded in half, typically lengthwise, bringing the bottom edge to the top or leading edge and creating a pocket for the hair to absorb and react to the coloring chemicals. The foil surface may have or be prepared with a tacky surface or other means to provide the necessary adhesion. The liquid chemical mixture also acts as an adhesive to maintain the foil in its folded position. As previously described, the trailing end or sealing section of the foil that is folded over on to the leading edge end of the foil may be transparent. In some embodiments, the whole sheet of the foil may be transparent as well.

When all of the foils have been attached to the head of the subject, the coloring chemicals applied, and the foils folded, the subject may be adorned with a significant number of foils.

Finally, depending on the chemical mixture used and the calculated processing time for the necessary reaction within a foil, each foil is removed. The stylist may simply wait a certain time, based on experience, for the coloring to work to the degree required. Alternatively, the curing process may be accelerated by the application of heat. Heat from a hair dryer or heat lamp may be used in this regard.

The FIGS. 6a and 6b embodiment of the foil with its reservoir 41 typifies a home use embodiment, incorporating the correct amount of chemical into each foil for less skillful or inexperienced users. The method for using this embodiment requires the user to moisten the foam pad with a brush and a wetting agent, preferably water but non-aqueous fluids may be used, to bring the chemical contents to a workable consistency. The user then paints the coloring chemicals onto the hair strands using the same brush. In some embodiments, the foam pad contains already moistened mixtures of bleach or color, sealed with a peel-off film, so that moistening is not necessary. This embodiment may also be attractive for use in some commercial environments.

When the hair strands have been sufficiently saturated with the coloring the foil is folded as described previously. The foam pad does not prevent the folded foil from remaining folded and in place, attached to the hair strands within.

There are numerous other embodiments of the invention. For example, there is a hair foil for use in hair coloring procedures consisting of a sheet of foil material having at least one pinked edge. A pinked edge in the context of this disclosure includes any edge design having a regular pattern of slots, V's, channels or like variations in the edge line through which strands of the underlying combed hair may be accessible for picking and pulling. The sheet itself may be between about 2 and 6 inches wide and between 4 and 12 inches long. There may be at least one hair anchor strip applied to one side of the foil along the pinked edge. The hair anchor strip may be aligned with the pinked leading edge.

The sheet may have an upper surface suitable for application of chemicals and conducting a chemical hair treatment process, and an underside surface suitable for contacting the underlying hair and scalp. The hair anchor strip may be attached or configured to be on either surface of the foil, near or at the leading edge. There may be one or more flaps or folds in the sheet, such as a push flap on the upper surface of the sheet oriented parallel to and proximate the leading edge, folded away from the leading edge so as to form a slot within or fold under which a hand tool such as a comb handle may be inserted from either side for urging the foil forward towards the scalp and hair scalp.

At least a portion of the upper surface of the sheet may be tacky or otherwise treated such that strands of hair are easily adhered to it. The foil material, or a portion or section of the foil, may consist of flexible transparent material. The sheet of foil may be configured with shoulder cut outs on the two corners at each end of the leading edge, providing a portion of the sheet that is wider than the leading edge.

The hair anchor strip may be or use one component of a hook and loop fastener system, or be configured with or fabricated as an analogous planar array of short, small barbed or hooked teeth, preferably plastic or semi-rigid in nature, that will engage readily with the combed hair on a subject's scalp and hold until purposely extracted with lifting and/or pulling force in the same direction as the underlying hair is combed. The term hook and loop fastener material, or hooked surface, as used herein includes all analogous structures that present a rigid or flexible planar array of short, barbed or hook-like teeth readily entangling and engaging upon contact with a body or individual strands of elongate hairs or fibers such as a loosely assembled fabric structure or the combed hair, or picked strands of hair of a person or other subject.

Another example is a hair processing appliance or tool for use in restraining a section of long hair to a desired place on the scalp, consisting of a base plate that may be flexible or rigid, the underside of which is at least partially configured with a hair anchor strip such as one component of a hook and loop fastener system, with at least a portion of the edge of the base plate being configured with a pinked pattern. There may be a top side hair clip or other hair holding device incorporated into the tool. The tool may accept attachment along one edge of a sheet of hair foil material, as by a tacky surface, elongate slot or clip, so that the tool becomes or can be used in the same manner as a foil of the invention.

Other examples of the invention include manual or automated methods for making hair foils for use in chemical hair treatment procedures, which may include the steps of using a continuous web of foil material with a width of at least twice the length of the sheet of a finished hair foil, applying a continuous strip of hair anchoring material to at least one side at about the center of the continuous web, splitting the web at about the center into two parts or webs, and cutting each web into individual foils.

Still yet more examples are manual or automated methods for making hair foils consisting of the steps of using a continuous web of foil material with a width of at least twice the length of the sheet of a finished hair foil, where the web has an underside intended for placement against the combed hair of the scalp and an upper side intended for application of chemicals, folding a set of four adjacent fold lines into the center of the continuous web of foil material with the first fold turning back on the upper side, and the second fold turning back on the underside, the third fold turning back on the underside, and the fourth fold turning back on the upper side so as to place the first and fourth fold lines between the second and third fold lines. Then or concurrently applying a continuous strip of hair anchoring material to the underside of the continuous web so as to cover both the first and forth fold lines, splitting the web between the first and fourth fold lines into two parts so as to split the continuous strip of hair anchoring material, and cutting each part into individual hair foils. The splitting step may be done with a pinking split so as to yield a pinked edge on each of the parts.

A further example is a hair foil consisting of a flexible sheet with a leading edge, positionable on the combed hair of a subject's scalp, with a hair anchor strip on the underside of the sheet adherable to the combed hair, where selected strands of the combed hair are removable from under the sheet through the hair anchor strip by picking and pulling the selected hair strands from along the leading edge. The sheet may incorporate at least one flap or fold, the hinge line of which is parallel to the leading edge. The hair anchor strip may be an array of short, barbed teeth engagable with the combed hair, or other analogous structure.

A yet further example is a hair holding appliance consisting of a base plate, the underside of which is configured with a hooked surface. The topside may be likewise configured with a hooked surface. The topside may be configured with a hair clip. The appliance may have means for attaching a sheet of hair foil material.

A still further example of the invention is a component of a hair holding system consisting of a continuous length of hair holding base plate material, the underside of which is configured with a hooked surface, and the edge of the base plate material is configured with a pinked edge pattern, whereby useful unit lengths of the hair holding base plate material may be cut from the continuous length, as for use as an appliance or foil of the invention. The top side of the base plate material may be configured with a tacky surface suitable for attachment of a foil blank.

While the invention has been described with reference to specific embodiments, it will be apparent that other and various embodiments, combinations of features, improvements and modifications may be made within the purview of the invention without departing from the scope of the invention defined in the appended claims.

I claim:

1. A hair foil for use in chemical hair treatment procedures, comprising
    a sheet of foil material having an upper surface for application of chemicals, an underside surface for contacting the scalp, and a pinked leading edge,
    at least one hooked surface hair anchor strip applied to said underside surface proximate said pinked leading edge,
    said sheet of foil configured with shoulder cut outs on each end of said pinked leading edge whereby a portion of said sheet is wider than said leading edge, and
    said hair foil further comprising a push flap on the upper surface of said sheet oriented parallel to and proximate to said pinked leading edge and folded away from said pinked leading edge such that a tool may be positioned at any point thereunder for urging said foil forward.

2. A hair foil according to claim 1, said sheet being between 2 and 6 inches wide and between 4 and 12 inches long.

3. A hair foil for use in chemical hair treatments comprising:
    a flexible sheet with a leading edge, positionable on the hair of a subject's scalp,
    a hooked surface hair anchor strip on the underside of said sheet adherable to said hair, wherein said leading edge being a pinked leading edge, said hair anchor strip comprising an array of short, barbed teeth engagable with said hair,
    said sheet incorporating at least one push flap, a hinge line of which is parallel to said leading edge,
    said push flap being folded away from the leading edge such that a tool may be positioned at any point thereunder for urging said foil forward.

4. A hair foil for use in chemical hair treatments according to claim 3, said sheet being configured with shoulder cut outs on each end of said leading edge whereby a portion of said sheet is wider than said leading edge.

* * * * *